US006847456B2

(12) United States Patent
Yang et al.

(10) Patent No.: US 6,847,456 B2
(45) Date of Patent: Jan. 25, 2005

(54) METHODS AND SYSTEMS USING FIELD-BASED LIGHT SCATTERING SPECTROSCOPY

(75) Inventors: Changhuei Yang, Cambridge, MA (US); Adam P. Wax, Boston, MA (US); Lev T. Perelman, Brookline, MA (US); Ramachandra R. Dasari, Lexington, MA (US); Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 101 days.

(21) Appl. No.: 09/844,286

(22) Filed: Apr. 27, 2001

(65) Prior Publication Data

US 2002/0101593 A1 Aug. 1, 2002

Related U.S. Application Data

(60) Provisional application No. 60/200,187, filed on Apr. 28, 2000.

(51) Int. Cl.[7] .................................................. G01B 9/02
(52) U.S. Cl. ....................................... 356/489; 356/511
(58) Field of Search ................................ 356/489, 484, 356/485, 517, 479, 497, 503

(56) References Cited

U.S. PATENT DOCUMENTS

| | | | |
|---|---|---|---|
| 4,080,264 A | | 3/1978 | Cohen et al. ............. 195/103.5 |
| 5,410,413 A | | 4/1995 | Sela ........................... 356/446 |
| 5,481,360 A | * | 1/1996 | Fujita ......................... 356/489 |
| 5,565,986 A | | 10/1996 | Knüttel ....................... 356/346 |
| 5,627,666 A | | 5/1997 | Sharp et al. .................. 349/74 |
| 5,838,485 A | * | 11/1998 | de Groot et al. ............ 356/484 |
| 5,919,140 A | | 7/1999 | Perelman et al. ........... 600/476 |
| 5,943,129 A | | 8/1999 | Hoyt et al. .................. 356/318 |
| 6,015,969 A | * | 1/2000 | Nathel et al. .......... 250/227.27 |
| 6,091,496 A | | 7/2000 | Hill ............................. 356/351 |

FOREIGN PATENT DOCUMENTS

| | | |
|---|---|---|
| EP | 1132731 A | 9/2001 |
| WO | WO 98/38907 | 9/1998 |

OTHER PUBLICATIONS

Izatt, J.A., et al., "Optical Coherence Tomography for Bio-diagnostics", *Optics and Photonics News*, 41–65, (1997).

Yang, C., et al., "Spatial coherence of forward–scattered light in a turbid medium", *J. Opt. Soc. Am.*, 16(4):866–871 (1999).

Huang, D., et al., "Optical Coherence Tomography," *Science*, 254:1178–1181 (1991).

Wax, A. et al., "Optical heterodyne imaging and Wigner phase space distributions", *J. Opt. Soc. Am*, 1427–1429 (1996).

Wax, A. et al., "Measurement of smoothed Wigner Phase–space distributions for small–angle scattering in a turbid medium", *J. Opt. Soc. Am*, 15(7):1896–1908 (1998).

Wax, A. et al., "Optical phase–space distributions for low–coherence light", *Optics Letters*, 24(17):1180–1190 (1999).

(List continued on next page.)

*Primary Examiner*—Zandrav Smith
*Assistant Examiner*—Andrew H. Lee
(74) *Attorney, Agent, or Firm*—Weingarten, Schurgin, Gagnebin & Lebovici LLP (57) ABSTRACT

The present invention relates to systems and methods of field-based light scattering spectroscopy. These systems and methods provide for the diagnosis of tissue by measuring the size and distribution of cellular characteristics. Field based measurements provide phase information resulting from the interaction of scatterers within the material and the incident wavefront. These measurements can be used to provide three dimensional images of tissue.

27 Claims, 8 Drawing Sheets

OTHER PUBLICATIONS

Wax, A. et al., "Characterizing the Coherence of Broadband Sources Using Optical Phases Space Contours", *J. Bio. Opt.*, 4(4):482–489 (1999).

Perelman, L.T., et al., "Observation of Periodic Fine Structure in Reflectance from Biological Tissue: A New Technique for Measuring Nuclear Size Distribution", Am. Physical Soc., 80(3):627–630 (1998).

Eda, H., et al., "Multichannel time–resolved optical tomographic imaging system," *Am. Inst. Phy.*, 70(9):3595–3602 (1999).

Hebden, J.C., et al., "Simultaneous reconstruction of absorption and scattering images by multichannel measurement of purely temporal data", *Optics Letters*, 24(8):534–536 (1999).

Barbour, R.L., et al., "Imaging of Diffusing Media by a Progressive Iterative Backprojection Method Using Time–Domain Data", *SPIE*, 1641:21–34 (1992).

Ueda, Y., et al., "Average Value Method: A New Approach to Practical Optical Computed Tomography for a Turbid Medium Such as Human Tissue", *Jpn. J. Appl. Phys.*

Barbour, R.L., et al., "Imaging of Subsurface Regions of Random Media by Remote Sensing", *SPIE*, 1431:192–203 (1991).

Chen, K., et al., "Optical computed tomography in a turbid medium using early arriving photons", *J. Bio. Optics, in Press* (2000).

Yang, C., et al. "Feasibility of Field–based Light Scattering Spectroscopy", Offshore, Industrial Publications, Conroe, TX, 5(2):138–143 (2000); XP001051328 ISSN: 0030–0608.

Izatt, J.A. et al., "Optical Coherence Tomography and Microscopy in Gastrointestinal Tissues." *IEEE Journal of Slected Topics in Quantum Electronics*, 2(4):1017–1028 (1996), XP002186809.

* cited by examiner

METHODS AND SYSTEMS USING FIELD-BASED LIGHT SCATTERING SPECTROSCOPY

RELATED APPLICATIONS

This application claims the benefit of U.S. Application No. 60/200,187 filed Apr. 28, 2000. The entire teachings of the above application is incorporated herein by reference.

GOVERNMENT SUPPORT

The invention was supported, in whole or in part, by a grant P41-RR02594 from the National Institutes for Health. The Government has certain rights in the invention.

BACKGROUND OF THE INVENTION

Optical imaging techniques have been shown to be useful diagnostic tools for a number of biomedical applications. Increasingly, the structure of biological tissue is being studied using the interaction of the tissue with light. For example, using light scattering spectroscopy (LSS) the size and index of refraction of scatterers comparable in size to the wavelength of light are profiled by measuring the periodicity of the spectra of reflected light. In standard pathological analysis, sensitivity to variations in the size and index of refraction of cell nuclei can give indications of abnormal cell activity. For example, pre-cancerous epithelial cells exhibit nuclear enlargement.

Generally, obtaining spectroscopic information from tissue in vivo is difficult as light scattered from surrounding tissues often obscures the desired optical signal. This can be overcome through a combination of spectroscopy with a biomedical imaging techniques which provide the ability to isolate the light scattered from a specific portion of a biological sample. For example, light scattering techniques have been used during endoscopic procedures to measure the size distribution of cell nuclei and refractive index changes in the epithelial linings of the body. In these studies, the intensity of white light back-scattered from the tissue is collected via an optical fiber probe and spectrally analyzed. The cell nuclei behave like Mie scatterers. Such particles exhibit periodic intensity variations with wavelength that are proportional to their sizes (typically 5–15 $\mu$m) and relative refractive indices. Thus light scattering spectroscopy (LSS) is of interest because changes in the size of cell nuclei and their chromatin content (related to refractive index) are primary indicators of dysplasia, the precursor of cancer, and treatment is most simple and effective when implemented at this early stage. However, intensity based LSS only provides a two-dimensional image.

Optical Coherence Tomography (OCT) is another technique that has been developed as a diagnostic tool for the study of biological tissue especially for noninvasive cross-sectional imaging in biological systems. OCT uses low-coherence interferometry to produce a three-dimensional image of optical scattering from internal tissue microstructures in a way that is analogous to ultrasonic pulse-echo imaging. OCT has longitudinal and lateral spatial resolutions of a few micrometers and can detect reflected signals as small as about $10^{-10}$ of the incident optical power.

In OCT, tissue is placed in a Michelson interferometer illuminated by a broadband light source. Due to the limited coherence length of the source (typically 10–15 $\mu$m), light returning from the interferometer reference arm and light backscattered by internal sample reflections interferes constructively or destructively only when the interferometer arm optical path lengths are matched to within the source coherence length. Scanning the reference arm length generates a localized interference pattern to appear in the detector current for every internal sample reflection as a function of depth along the sample arm beam. A sample containing many reflection sites distributed along its depth (such as biological tissue) generates a detector current that contains the sum of multiple, overlapping copies of this interference pattern. A map of tissue reflectivity versus depth (called an A-Scan) is obtained by scanning the reference mirror while recording the detector current. The envelope, or outline of the detector current, may be recorded with high dynamic range by scanning the reference mirror at fixed velocity, while demodulating the detector current at the resulting Doppler frequency. Cross-sectional images of tissue backscatter (called B-Scans) are acquired by collecting sequential A-scans while scanning the probe beam across the tissue surface. The resulting two-dimensional datasets are plotted as gray-scale or false-color images. However, OCT does not provide a functional image as the resultant resolution does not provide an image of the cell nuclei, whose size, shape and other characteristics can reveal abnormal cell activity.

SUMMARY OF THE INVENTION

The present invention relates to systems and methods employing field-based light scattering spectroscopy to provide three-dimensional images and for determining physical characteristics of biological tissue. The three-dimensional images provide information regarding the characteristics of cellular or other structures including, for example, size, shape, texture of the cell nuclei as well as cellular dynamics which can include motility and chaos. Field-based LSS systems incorporate spectroscopic information into a low coherence interferometer system. This field-based type of LSS can be differentiated from intensity-based LSS as it is able to isolate small regions of a biological sample for study, and yields information regarding the phase, as well as the amplitude, of the scattered field. Because field-based LSS measures phase of the wavefront, and wavefront uniformity, as well as providing a high degree of spatial resolution, field-based LSS can measure the shape and spatial distribution of cell nuclei along with size and refractive index of the nuclei. To ascertain the shape of cell nuclei, measurements of the scattered light's amplitude wavefront, phase wavefront, and wavefront non-uniformity are combined. Spatial distribution of cell nuclei is ascertained by three dimensional profiling which allows for imaging of cell nuclei density over the probed region.

In a preferred embodiment, the field-based LSS system includes an angular light scattering system which measures both the position and angular distribution of a light field. Angular distributions provide information regarding variations in phase front uniformity (coherence of the scattered light) as well as indicate size of the scatterer. This system can include a light source such as a laser and an optical system that provides spatially coherent light having first and second wavelength components that are aligned to illuminate a region of interest of the material or tissue under study. A reference beam having both first and second wavelengths is also directed through the optical system along an optical path having an adjustable path length. An actuator is used to vary the path length at a selected speed such that detection of the reference beam and the light returning from the material under examination can generate a heterodyne signal which is and analyzed to determine selected characteristics of the material.

In another preferred embodiment, the field-based LSS system includes a dynamic light scattering system to measure dynamic properties of tissue structure such as cell nuclei within a small selected region by combining field-based LSS with temporal measurements. Motions of small objects can be detected by scattering of laser light through examination of its statistical properties such as, for example, autocorrelation function and power spectra.

A preferred embodiment of the invention involves a system for fiber optic delivery and a collection of light from tissue to provide real time diagnostic measurements either in vitro or in vivo. A preferred method of using the system involves analysis of the collected data by storing the data in memory of computer and comparing the collected data with reference data previously stored in electronic memory or database.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
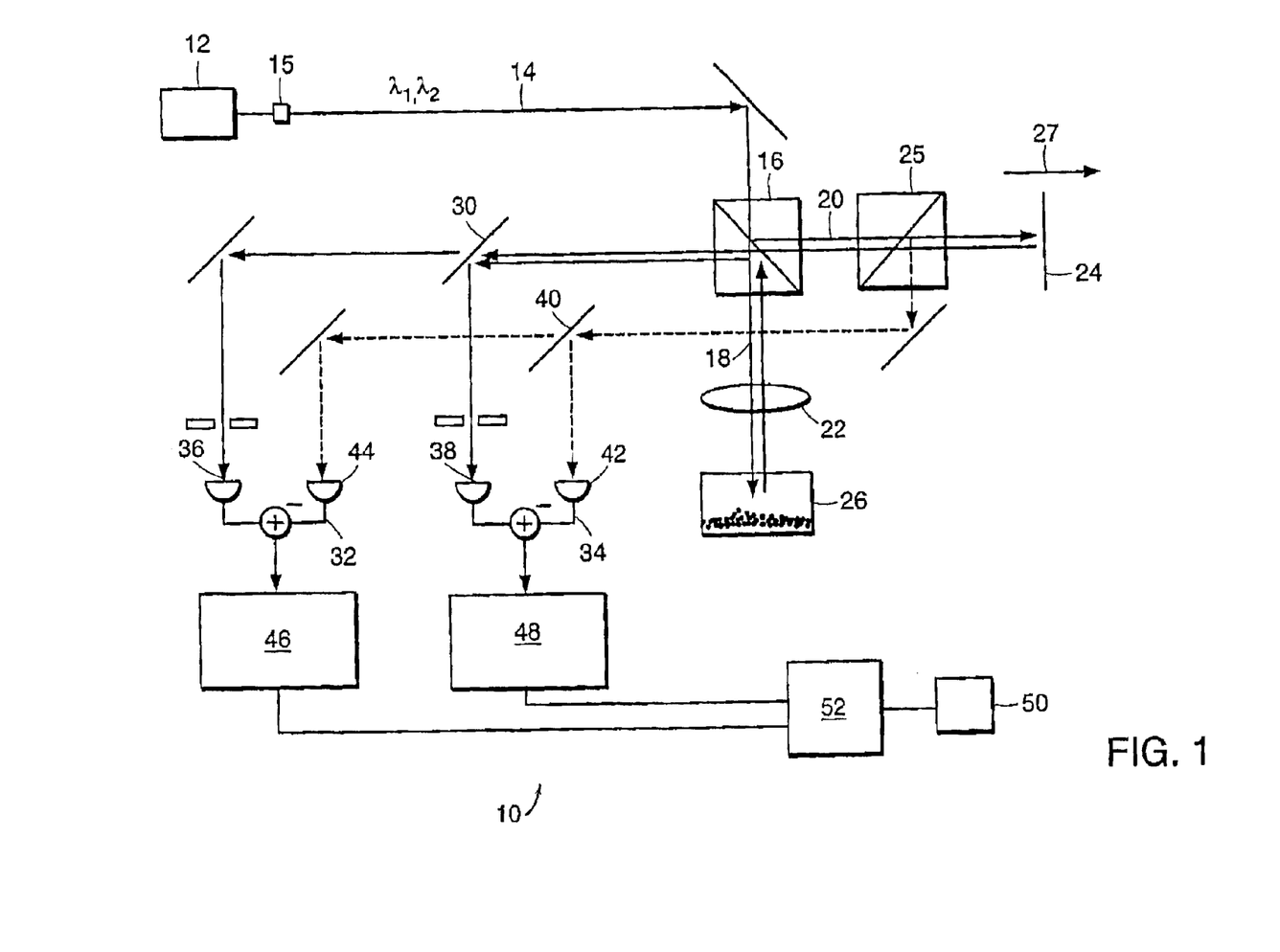
FIG. 1 illustrates a schematic diagram of a system using field-based light scattering spectroscopy in accordance with the present invention.

Referring to FIG. 1, a preferred embodiment of a field based LSS system 10 is illustrated, including a Michelson interferometer with two low-coherence light sources. In this particular embodiment, a Coherent MIRA Ti:sapphire laser 12 operating in femtosecond mode (150 fs) produces 800 nm light. The measured coherence length is about 30 µm. A portion of this light is handled by converter 15 such that it is split off and up-converted to 400 nm by means of a CSK Optronics LBO second harmonic generation crystal. Note that two or more separate light sources can be used to provide the two or more wavelengths used for particular measurements. The converted light is then recombined with the original beam. There is preferably substantial overlap (i.e., greater than 50% and preferably greater than 80%) between the two wavelength components. Reduced overlap will increase the scan time to illuminate a given surface are or volume. The combined beam 14 is then divided by a beam-splitter 16 into a probe beam 18 and a reference beam 20. Alternatively, a single beam can be used with a variable wavelength source.

The probe beam 18 is focused onto the sample by means of a 12.7 mm focal length achromatic lens 22. The powers of the 400 and 800 nm components at the sample are 14 and 5.5 mW, respectively. The beam waists at the lens are 1.1 and 2.1 mm (FWHM), resulting in beam waists at the focal point of 5.9 and 6.2 µm, and the Rayleigh lengths of 270 and 150 µm, respectively. As the coherence length is shorter than the Rayleigh lengths, the probe region can be approximately represented as a cylinder. The calculated beam overlap within this region is 98%, thus insuring that the same particles within the material 26 are illuminated simultaneously at both wavelengths.

The reference beam 20 is reflected from a mirror 24 moving along linear axis 27 at a constant speed, inducing Doppler shifts of 14.6 and 7.3 kHz at 400 and 800 nm, respectively. It is then recombined with the probe light backscattered from the material 26 and transmitted to a dichroic mirror 30, which separates the 400 and 800 nm components and delivers them to separate auto-balanced photoreceivers 32, 34 (New Focus 2007). Apertures 36, 38 are positioned in front of the detectors to limit the amount of collected light. In this particular embodiment the apertures have a radius of 0.9 mm. The distance from the collection lens 22 to the detectors is about 50 cm. A portion of the reference beam is separated with a second beamsplitter 25 and sent to a second dichroic mirror 40. The two output components from the mirror are delivered to the reference ports 42, 44 of the photoreceivers. This serves to cancel power fluctuations at the two wavelengths.

The heterodyne signal at each wavelength, which results from the interference of the back-scattered probe beam and the appropriate Doppler-shifted reference beam, is detected by the photoreceiver. Each signal is measured using a Stanford Research 830 lock-in amplifier array 46, 48. The magnitude of the heterodyne signal is displayed on a display 50 or oscilloscope and/or recorded by a computer 52.

In an example of a measurement of a sample in accordance with the invention, a cuvette with a thin layer of clear gelatin about 3 mm thick is followed by a layer of polystyrene microspheres suspended in gelatin. The probe beam enters the sample through the first layer and is brought to a focus at the interface between the first and the second layers. The two layers have the same refractive index, which ensures that there is no reflective interface between them. Therefore, any heterodyne signal observed can be attributed solely to scattering from the microspheres.

The polystyrene microspheres range from 0.53 to 6.09 µm and can be obtained from Bangs Laboratories, Polysciences Inc. and Spherotech Inc. The volume concentration of microspheres within the second layer is maintained at 1.3% for these samples. Based on an illumination volume of about 850 µm³, as defined by the waist at the focus of the probe beam and its coherence length, the average number of microspheres illuminated ranges from 140 for the 0.535 µm microspheres to 0.1 for the 6.1 µm microspheres. The refractive index ratio of the microspheres to the gelatin is measured independently to be 1.19±0.01. To account for attenuation and absorption of the probe beam in the first layer of gelatin, the results are normalized using heterodyne signals from a cuvette in which the second layer of gelatin is replaced by a mirror.

The amplitude of the measured heterodyne signal depends primarily on three factors: the number of microspheres illuminated, their positions within the probe beam, and the amount of back scattering they produce. Errors that may arise from the first two factors include that they can potentially skew the measurement and mask the periodic structure of the light scattering spectrum. These contributions can be minimized or eliminated by aligning the 400 and 800 nm beam components and employing approximately equal beam waists at the focus, as described above. This ensures that the beam components at both wavelengths illuminate the same region of the sample, and thus the same microspheres. Therefore, by taking the ratio of the signals at the two wavelengths, any dependence on the number and positions of the microspheres are normalized out.

In general, the heterodyne signal from the interference of the reflection from a group of scatterers with a reference beam can be expressed as:

$$|[2E_r(\vec{\rho})E_T(\vec{\rho})e^{i\psi_T(\vec{\rho})}]_{\vec{\rho}} x x e^{i\Delta\omega t}| = |[2E_r(\vec{\rho})E_T(\vec{\rho})e^{i\psi_T(\vec{\rho})}]_{\vec{\rho}}| \quad (1a)$$

with $E_r(\vec{\rho})$ the electric field of the reference beam incident on the detector, $\vec{\rho}$ the spatial coordinate on the detector's surface, $E_T(\vec{\rho})$ is the amplitude component of the signal electric field which is polarized in the same direction as the reference beam. Henceforth, all discussion of electric fields refer to those polarized in the plane of the reference beam's polarization. The symbol $\Delta\omega$ to denotes the heterodyne frequency, t represents time, and $\psi_T(\vec{\rho})$ the associated phase shift of the signal field to the reference field. $[\ldots]_{\vec{\rho}}$ indicates averaging over the detector area and $|\ldots|$ denotes amplitude.

$$\left|[2E_r(\vec{\rho})E_T(\vec{\rho})e^{i\psi_T(\vec{\rho})}]_{\vec{\rho}}\right| = \left|\sum_{j=1}^{\infty}\sum_{i=1}^{\infty}[2E_r(\vec{\rho})E_{j,i}(\vec{\rho})e^{i\psi_{j,i}(\vec{\rho})}]_{\vec{\rho}}\right|, \quad (1b)$$

Where $\psi_{j,i}(\vec{\rho})$ denotes the amplitude of the scattered electric field associated with the ith trajectory which has undergone exactly j scattering events in the sample, and $\psi_{j,i}(\vec{\rho})$ the associated phase.

Each term on the right hand side of Eq. (1) can be rewritten as:

$$[2E_r(\vec{\rho})E_{j,i}(\vec{\rho})e^{i\psi_{j,i}(\vec{\rho})}]_{\vec{\rho}} = a_{j,i}\bar{E}_r\bar{E}_{j,i}e^{i\bar{\psi}_{j,i}} \quad (2)$$

where $\bar{E}_r$ and $\bar{E}_{j,i}$ denote the root mean square averages of $E_r(\vec{\rho})$ and $E_{j,i}(\vec{\rho})$ over the detector areas, and $\bar{\psi}_{j,i}(\vec{\rho})$ the effective average phase shift. The phase and amplitude of the scattered field must be averaged over the detector since light incident on scatterers will be scattered in different amounts at different angles. The reference field is represented as having a Gaussian transverse spatial variation across the detector. The quantity $a_{j,i}$ is the spatial coherence factor. It measures the uniformity of $\psi_{j,i}(\vec{\rho})$, as well as the correlation of $E_{j,i}(\vec{\rho})$ with $E_r(\vec{\rho})$. Its maximum value, 2, occurs when $\psi_{j,i}(\vec{\rho})$ is constant over the detector surface, and $E_{j,i}(\vec{\rho})$ is identical in profile to $E_r(\vec{\rho})$. Note that $\bar{E}_r$ and $\bar{E}_{j,i}$ are simply the square roots of the average reference intensity and scattered intensity at the detector, respectively.

Note that $a_{j,i}$ decreases very rapidly with increasing values of j. This indicates that a heterodyne measurement strongly favors the detection of singly scattered light over multiply scattered light, provided that the two are present in comparable amounts. Such is the case for light scattered near the surface of a turbid medium such as tissue. Thus, in our case the measured heterodyne signal can be approximated by the terms associated with the $a_{1,i}$'s in Eq. (1b):

$$\left|[2E_r(\vec{\rho})E_T(\vec{\rho})e^{i\psi_T(\vec{\rho})}]_{\vec{\rho}}\right| \approx \bar{E}_r \left|\sum_{i=1}^{N} a_{1,i}\bar{E}_{1,i}e^{i\bar{\psi}_{1,i}}\right|. \quad (3)$$

Note that since the number of trajectories with only one scattering event equals the number of scatterers illuminated, N, the summation in Eq. (3) is terminated at N.

The amplitude of the heterodyne signal can be evaluated from Eq. (3) as:

$$H = \left|[2E_r(\vec{\rho})E_T(\vec{\rho})e^{i\psi_T(\vec{\rho})}]_{\vec{\rho}}\right| \quad (4)$$

$$\approx \bar{E}_r \sqrt{\sum_{i=1}^{N}(a_{1,i}\bar{E}_{1,i})^2 + \sum_{i=1}^{N}\sum_{i'=1}^{N} a_{1,i}a_{1,i'}\bar{E}_{1,i}\bar{E}_{1,i'}\cos(\bar{\psi}_{1,i}-\bar{\psi}_{1,i'})}$$
$$i' \neq i$$

$$\approx \bar{E}_r \sqrt{\sum_{i=1}^{N}(a_{1,i}\bar{E}_{1,i})^2}$$

The cross terms in Eq. (4) are negligible if the $\bar{\psi}_{1,i}$'s are uncorrelated and the number of scatterers, N, in the probe region is large. The later requirement can be satisfied by averaging over a sufficient number of measurements taken at different points on the sample. The assumption that the $\bar{\psi}_{1,i}$'s are uncorrelated can be understood by noting that, in addition to the non-zero phase shift that the scattered light accumulates from the scatterers, there are additional random phase shifts due to the different round trip distances traversed by the light from scatterers at various depths. Given that the average spatial distance between neighboring scatterers in this measurement is at least 1.8 $\mu$m or about 2.2 times the 800 nm wavelength, the scattered light contributions are unlikely to be correlated.

For a medium with microspheres of diameter D illuminated by light of wavelength $\lambda$, we have an average field, $\bar{E}(\lambda,D)$, given by the square root of the average intensity of light per scatterer reaching the detector, $\bar{I}(\lambda,D)$. The root mean square ensemble average of the heterodyne signal from Eq. (4) can then be written as:

$$H(\lambda, D)|_{ensemble-rms} = \bar{E}_r \sqrt{\sum_{i=0}^{N}(a_{1,i}(\lambda, D, \bar{d}_i)\bar{E}_{1,i}(\lambda, D, \bar{d}_i))^2} \bigg| ensemble - rms \quad (5)$$

$$= \sqrt{N}\,\bar{E}_r\bar{a}(\lambda, D)\bar{E}_r(\lambda, D) = \sqrt{N}\,\bar{E}_r\bar{a}(\lambda, D)\sqrt{\bar{I}(\lambda, D)}$$

with $\vec{d}_i$, the displacement of the $i^{th}$ scatterer from the focal point. $\bar{a}(\lambda,D)$ is a defined quantity which accounts for the contributions of the $a_{j,i}(\lambda,D,\vec{d}_i)$'s to the ensemble averaged heterodyne signal. This is a fundamental characterization of the scattering process. Note that all quantities in Eq.(4) except $\bar{E}_r$ are functions of $\lambda$, D and $\vec{d}_i$; which is made explicit in Eq. (5).

In intensity-based LSS, N can be found by measuring the backscattered intensity at many wavelengths. More details regarding such measurements can be found in U.S. application Ser. No. 08/948,734 filed on Oct. 10, 1997. the entire contents of the referenced application being incorporated herein by reference. The same can be done in field-based LSS. Unfortunately, where the heterodyne signals are measured at only two wavelengths, N cannot be accurately determined. However, since the beam components at the two wavelengths are well aligned, and thus illuminate the same focal area, the same scatterers are simultaneously illuminated at both wavelengths in each measurement. To provide the ensemble average, make M individual measurements of H, each at a different beam position and sum, then sum over all the measurements at each wavelength. The ratio, R, of the two sums then eliminates any dependence on N:

$$R = \frac{\sqrt{\sum_{i=1}^{M} H_i^2(\lambda_1, D)}}{\sqrt{\sum_{i=1}^{M} H_i^2(\lambda_2, D)}} \approx \frac{\bar{a}(\lambda_1, D)\sqrt{\bar{I}(\lambda_1, D)}}{\bar{a}(\lambda_2, D)\sqrt{\bar{I}(\lambda_2, D)}} \quad (6)$$

Note that in addition to the scattered intensity, $\bar{I}(\lambda,D)$, which determines the reflectance spectrum in a conventional LSS experiment, field-based LSS is also influenced by the wavelength-dependent spatial coherence factor, $\bar{a}(\lambda,D)$. This indicates that the field-based LSS spectrum differs from the intensity-based LSS spectrum.

The ensemble averaged quantity $$\bar{a}(\lambda, D)\sqrt{\bar{I}(\lambda, D)}$$

can be calculated from Mie scattering theory for spherical objects. First express the contribution to the heterodyne signal from a single scatterer at a displacement $\vec{d}_i$ from the focal point. This is given by:

$$H(\lambda, D, \vec{d}_i) = \left| \left[ 2E_r(\lambda, \vec{p})E_i(\lambda, \vec{d}_i) \frac{S(\lambda, D, \phi_i, \theta_i)}{kr} \right]_p \right|, \quad (7)$$

with $E_i(\lambda, \vec{d}_i)$ the electric field strength at the scatterer and $S(\lambda,D,\phi_i,\theta_i)$ the amplitude function in the plane of polarization of the reference and incident beam. (Note that, $S(\lambda,D,\phi_i,\theta_i)$ is a complex function.) In this notation, $\theta_i$ is the angle subtended from the vertical, defined as the direction of the probe beam's propagation, and $\phi_i$ is the angle in the plane normal to the vertical, with $\phi_i=0$ being along the direction of polarization. $\theta_i$ and $\phi_i$ can be related to $\vec{p}$ and $\vec{d}_i$ by geometrical optics. k is the optical wavenumber and r the distance from the scatterer to the detector. $S(\lambda,D,\phi_i,\theta_i)$ can, in turn, be expressed as:

$$S(\lambda,D,\phi_i,\theta_i) = \sin^2(\phi_i)S_1(\lambda,D,\theta_i) + \cos^2(\phi_i)S_2(\lambda, D, \theta_i), \quad (8)$$

with $S_1(\lambda,D,\theta_i)$ and $S_2(\lambda,D,\theta_i)$ the amplitude functions given by Mie theory for in-plane and out-of-plane scattering, relative to the scatterer.

From Eq. (4), the ensemble averaged quantity $$\bar{a}(\lambda, D)\sqrt{\bar{I}(\lambda, D)}$$

equals the root mean square ensemble average of the heterodyne signal associated with N=1. In other words, it can be expressed in terms of the single scatterer's heterodyne contribution:

$$\bar{a}(\lambda, D)\sqrt{\bar{I}(\lambda, D)} = \frac{1}{\bar{E}_r} H(\lambda, D, \vec{d}_i)_{ensemblerms} = \frac{1}{\bar{E}_r\sqrt{Q}} \sqrt{\sum_{all\ \vec{d}_i} H^2(\lambda, D, \vec{d}_i)} \quad (9)$$

where Q is the number of elements in the ensemble average.

Using this formulation, the predictions for R for microspheres ranging from 0.1 to 7.0 $\mu$m in diameter can be determined. The result is then averaged over a 5% variation in diameter, to account for the distribution of microsphere sizes in a given sample. This distribution is consistent with the size distribution given by the manufacturers.

Figure 2:
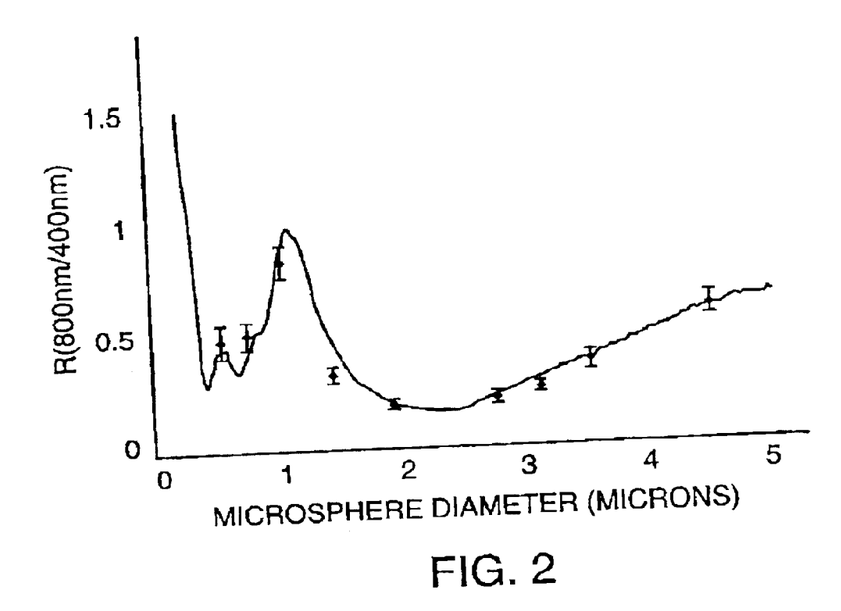
FIG. 2 graphically illustrates a theoretical fit of the data points measured in accordance with the present invention.

Measured data are plotted in FIG. 2. Each data point consists of 30 or 45 measurements taken at various sample positions. Averaging over scatterer position is determined by taking the root mean square of the measured heterodyne signal at each wavelength. The ration of the results, R, is then calculated and plotted.

The solid line in the plot is the theoretical fit. The fit was done using the procedure outlined above. In the fitting procedure, the aperture size of the detectors were free parameters. The best fit requires an aperture size of 0.7 mm in radius, instead of 0.9 mm, for the 400 nm measurements. This can be accounted for as a possible misalignment of the incoming beam at the detector, which can result in a smaller effective detection area.

The fit agrees well with the measurements for microspheres smaller than 5 microns in diameter. For the larger microsphere sizes the determination which is based on Mie scattering which assumes an incident plane wave field is not as accurate as the microsphere size becomes comparable to the beam waists (about 6 microns).

While both field-based and intensity-based LSS determine the size and relative refractive index of scatterers by measuring variations in scattering across the spectrum, field-based LSS differs from intensity-based LSS in two important ways. First, it is sensitive to phase front variations in the scattered wave, as well as to the intensity variations of the back-scattered light. Second, it permits greater localization of the region to be measured.

Single particle light scattering is characterized by the scattering amplitude, $S(\lambda,D,\phi,\theta)$, which is a complex function with a phase that varies with angular coordinates. This phase is not measured in intensity-based LSS. In contrast, field-based LSS is very sensitive to variations in phase. To illustrate this, consider a measurement with a plane wave incident field. The average scattering intensity from a single scatterer measured at the detector can then be expressed as:

$$\bar{I}(\lambda, D) = \frac{E_i^2}{k^2 r^2} \left[ |S(\lambda, D, \phi, \theta)|^2 \right]_p \quad (10)$$

From Eq. (7), a similar field-based LSS experiment in which the incident and reference fields are both plane waves will give a heterodyne signal of the form:

$$H(\lambda, D)^2 = \frac{4\overline{E}_r^2 \overline{E}_i^2}{k^2 r^2} \left| \langle [S(\lambda, D, \phi, \theta)]_p \rangle \right|^2. \quad (11)$$

Setting aside the average reference field intensity, $\overline{E}_r^2$ a subtle but important difference between these two expressions can be seen. In Eq. (10), the magnitude of $S(\lambda,D,\phi,\theta)$ is taken before averaging over the detector area, whereas in Eq. (11), the sequence of operations is reversed. Thus, phase variations become important in field-based LSS, and the measured signal is proportional to the degree of phase-front uniformity of the scattered light. As Mie theory shows, the phase front uniformity degrades as a function of $$\left(\frac{D}{\lambda}\right),$$

and so for a scatterer of a given size, there is more variation across the spectrum with field-based LSS than with intensity-based LSS. This, in turn, makes calculation of scatterer size easier and more sensitive.

The theory employs an ensemble-averaged spatial coherence factor, $\bar{a}(\lambda,D)$, to quantify the degree of phase front uniformity. Note that $\sigma(\lambda,D)$ is fundamentally related to $f(\lambda,D,\phi,\theta)$. By substituting Eqs. (10) and (11) into Eq. (5) and setting N=1 (as the above calculation is for a single scatterer), provides:

$$\bar{a}(\lambda, D) = 2\sqrt{\frac{\left|[S(\lambda, D, \phi, \theta)]_p\right|^2}{[|S(\lambda, D, \phi, \theta)|^2]_p}}. \quad (12)$$

Note that Eq. (12) is applicable only in situations where both the reference and incident fields are uniform, and are appropriately modified for non-uniform input fields.

To clarify the physical significance of $\bar{a}(\lambda,D)$, re-express Eqs. (10) and (11) in terms of the scattering cross section, $\sigma(\lambda,D)$, and phase function, $f(\lambda,D,\phi,\theta)$ [12]. The phase function is the normalized function which describes the angular intensity distribution of the scattered light. Since it is given by:

$$f(\lambda, D, \phi, \theta) = \frac{1}{k^2 \sigma(\lambda, D)} |S(\lambda, D, \phi, \theta)|^2, \quad (13)$$

express Eq. (10) as $$\bar{I}(\lambda, D) = \frac{\overline{E}_i^2}{r^2} \sigma(\lambda, D) [f(\lambda, D, \phi, \theta)]_p \quad (14)$$

The corresponding equation for the heterodyne signal, Eq. (11), can then be written in terms of $\bar{a}(\lambda,D)$ as:

$$H(\lambda, D)^2 = \frac{\overline{E}_r^2 \overline{E}_i^2}{r^2} \sigma(\lambda, D) \bar{a}^2(\lambda, D) [f(\lambda, D, \phi, \theta)]_p \quad (15)$$

In intensity-based light scattering measurements, the scattering cross-section, $\sigma(\lambda,D)$, and the anisotropy factor, $g(\lambda, D)$, are often used to characterize the scattering process. In contrast, specification of the scattering process in field-based light scattering requires a third parameter derived from $S(\lambda,D,\phi,\theta)$ the spatial coherence factor $\bar{a}(\lambda,D)$.

In addition to this sensitivity to phase variations, field-based LSS has the advantage of being able to localize a much smaller region for study. This localization can be achieved with low-coherence interferometric techniques, as exemplified by OCT. Spatial localization is limited by the coherence length, and a typical femtosecond laser beam can localize a region for study on the order of tens of microns. This opens the possibility of selectively probing each individual scatterer, such as a single cell nucleus, even when it is surrounded by other scatterers. The prospect of probing one scatterer at a time also simplifies the computations. For a single scatterer, the cross-terms in Eq. (4) will not be present, thereby eliminating the need to average over numerous samples. We also note that with the high sensitivity afforded by heterodyne techniques, the full-spectral response of field-based LSS may provide a means to resolve features of a scatterer that are considerably smaller than an optical wavelength.

Figure 3:
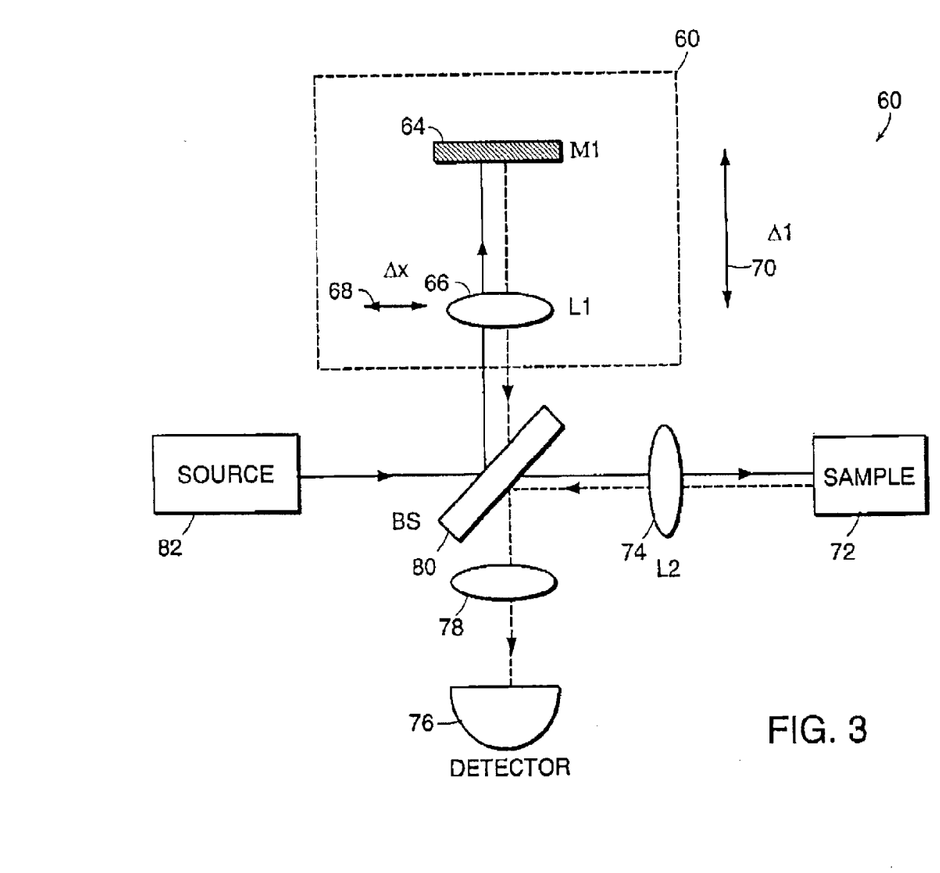
FIG. 3 illustrates a schematic diagram of a preferred embodiment of an angular light scattering system in accordance with the present invention.
Figure 4A:
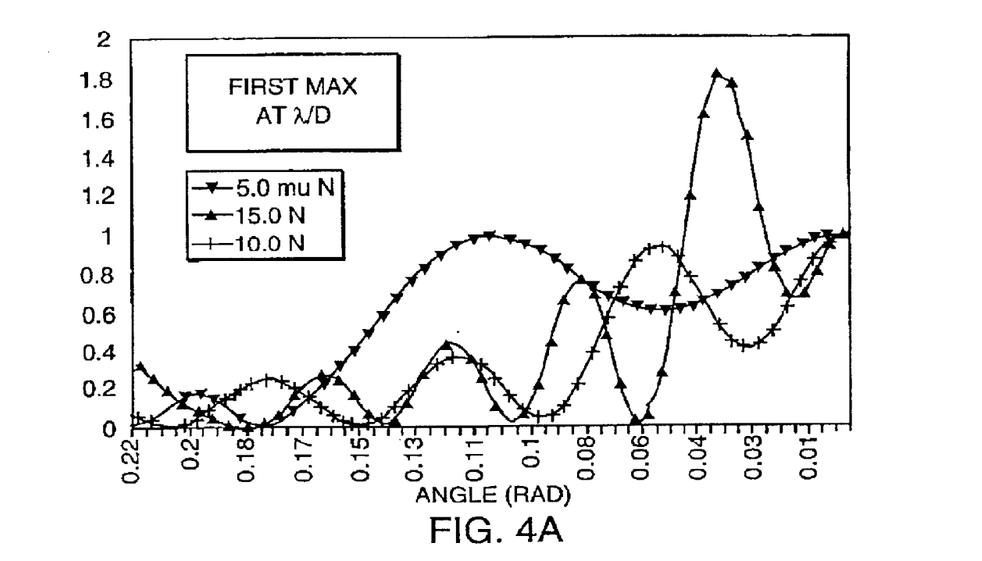
FIGS. 4A and 4B graphically illustrate theoretical angular distributions in accordance with the present invention.
Figure 4B:
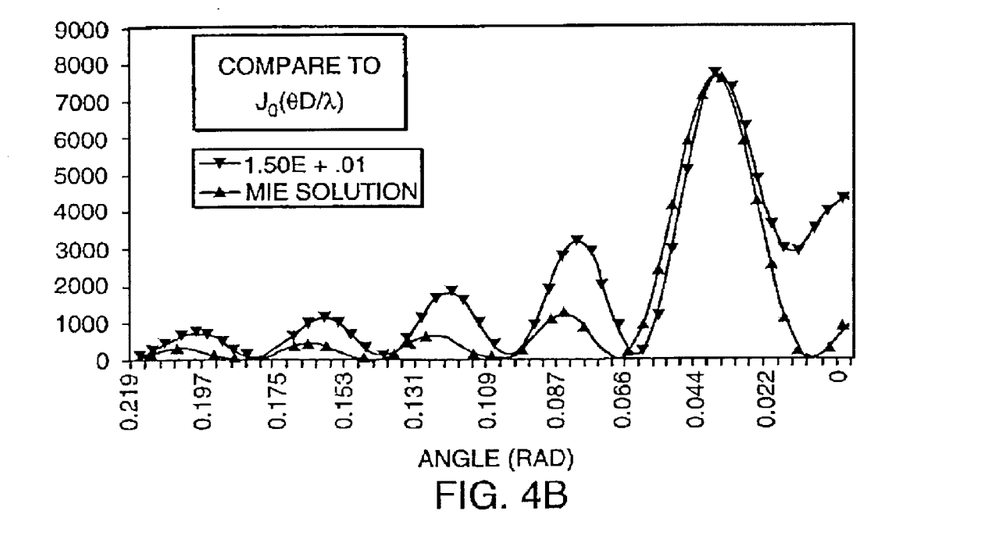
Figure 5A:
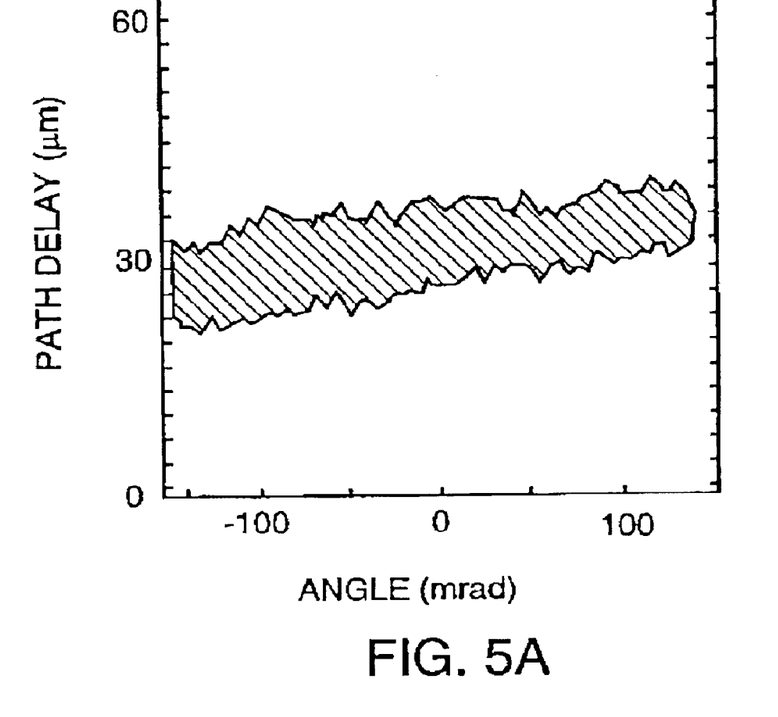
FIGS. 5A and 5B graphically illustrate path delay and intensity measurements related to the angular light scattering system in accordance with the present invention.
Figure 5B:
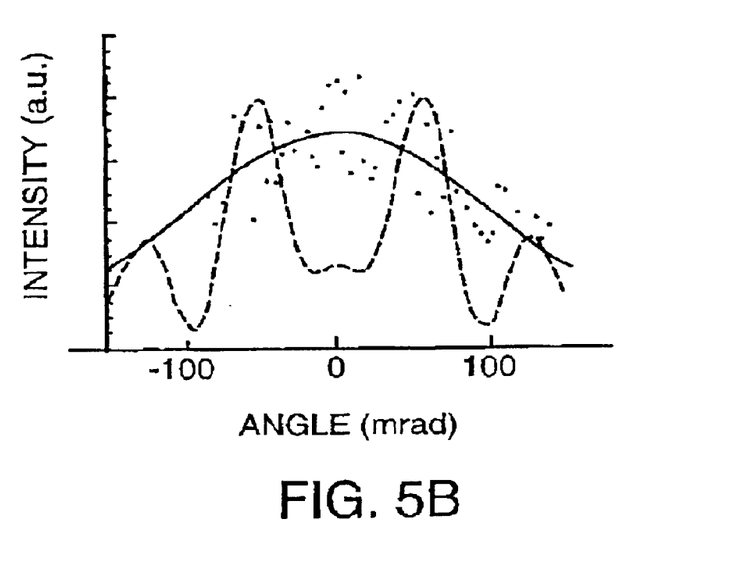

FIG. 3 illustrates another preferred embodiment 60 of the invention in which a source of light 82, a beamsplitter 80 which splits the light along two paths, a first path extends through lens 74 onto the tissue or object being measured and the second path is directed through lens 66 reflects off mirror 64 and is redirected through the beamsplitter 80 along with light returning from the object being measured through lens 78 to detector system 76. In this embodiment both the lens 66 and mirror 64 are displaced over a distance 70 during the measurement. Additionally, the lens 66 can be displaced in a second direction 68 to alter the direction of propagation. By scanning lens 66 and mirror 64 together as the angle of the reference field is scanned, the position of the reference field in the detector plan remains fixed. FIGS. 4A and 4B graphically illustrate the angular dependence of measurements made using the present invention. FIGS. 5A and 5B illustrate path delay and intensity measurement of a monolayer. The angular resolution of this measurement is about 0.45 mrad, and the longitudinal resolution is about 11.6 $\mu$m.

Figure 6:
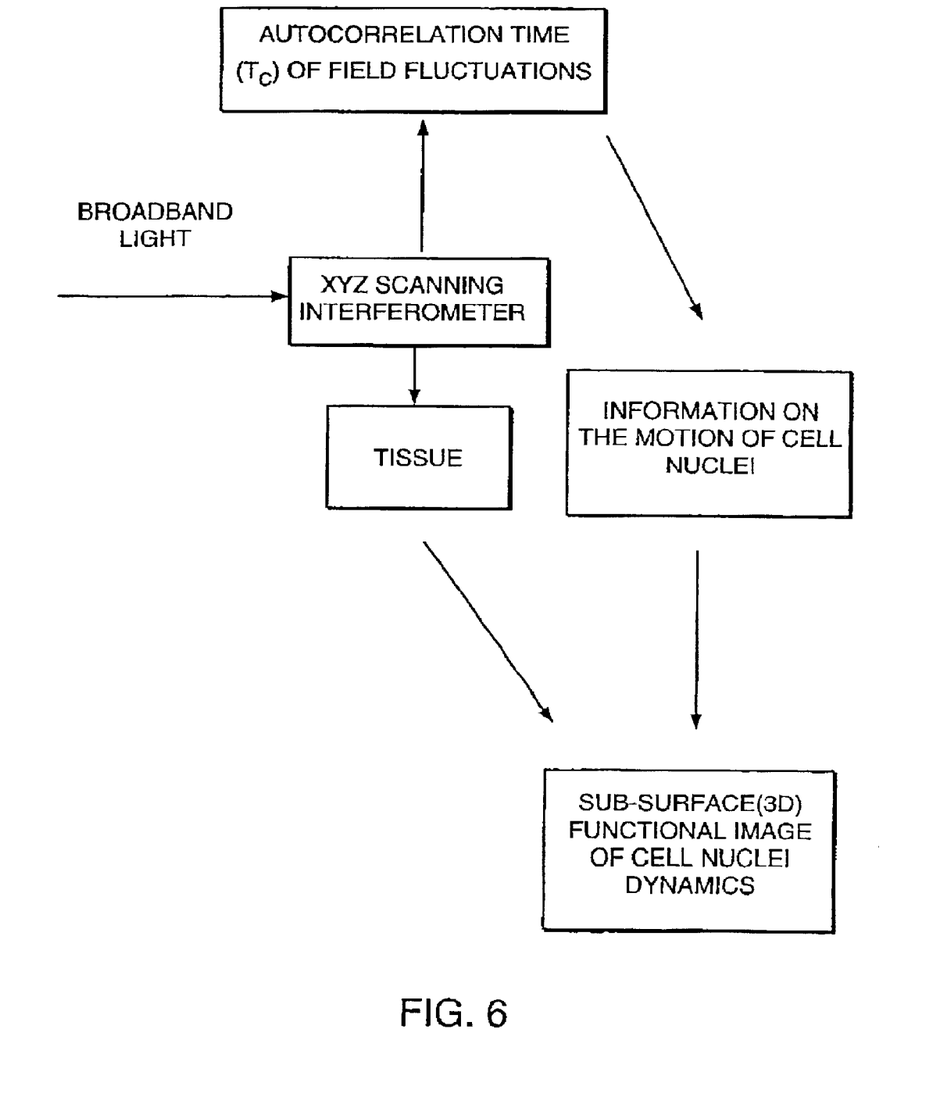
FIG. 6 illustrates a block diagram of a preferred embodiment of a dynamic light scattering spectroscopy system in accordance with the present invention.
Figure 7:
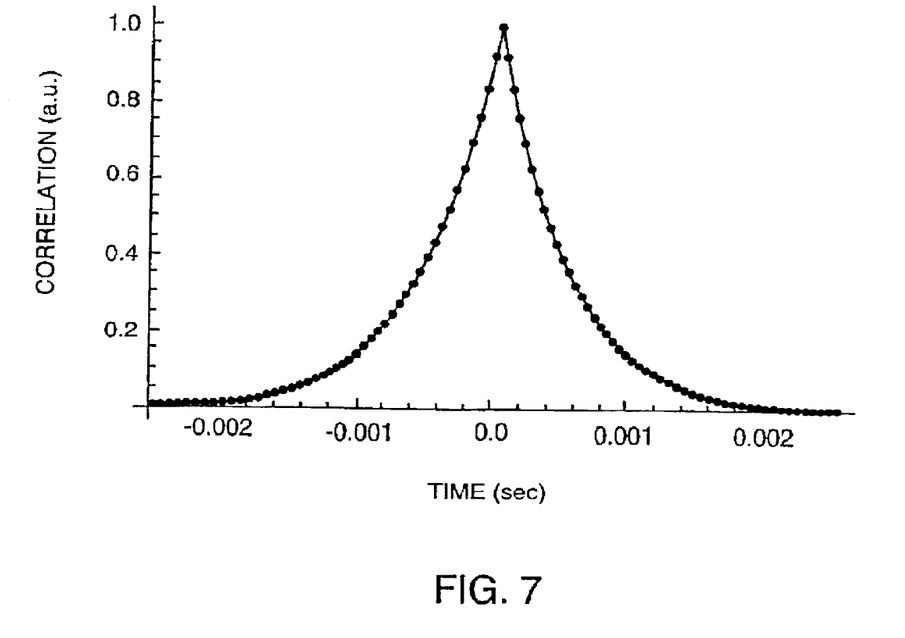
FIG. 7 graphically illustrates the correlation measurement related to the dynamic light scattering spectroscopy system in accordance with the present invention.

FIG. 6 schematically illustrates a process in which measurements employing autocorrelation methods provide information and images of changes in cellular or subcellular structures in tissue. FIG. 7 graphically illustrates the results of measurements of correlation in the intensity of light from a He—Ne laser scattered by a dilute suspension of beads. The autocorrelation time of 0.51 msec is consistent with multiple scattering of the light by 0.22 micron beads.

Figure 8:
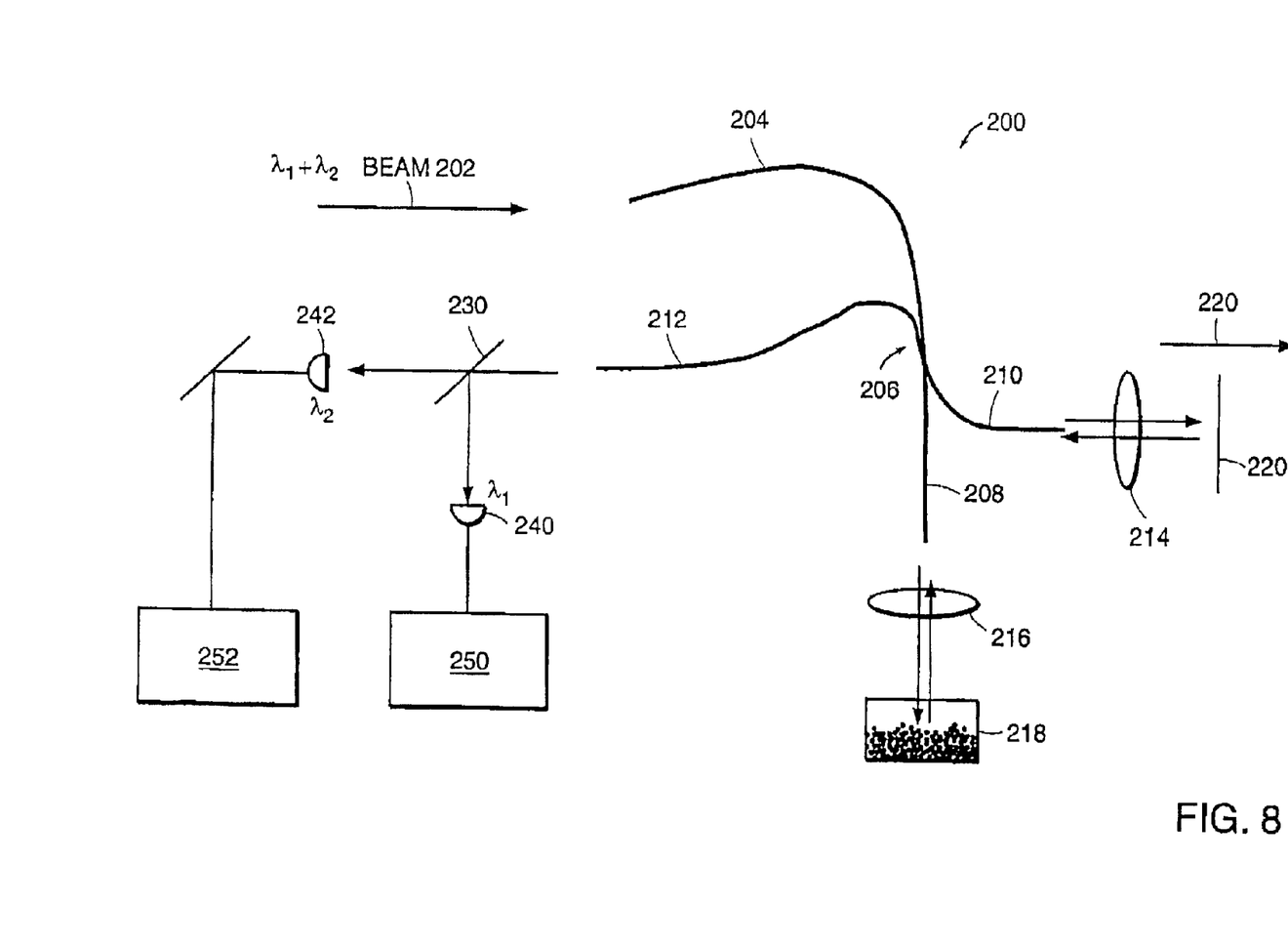
FIG. 8 schematically illustrates a fiber optic system used in conjunction with the present inventions.

Illustrated in connection with FIG. 8 is a fiber optic system 200 for light delivery and/or collection in conjunction with the light scattering spectroscopic systems and methods of the invention described previously. A light source provides a beam 202 that includes at least two wavelengths $\lambda_1$, $\lambda_2$ which are coupled to the proximal end of optical fiber 204. A beam splitter 206 incorporated into the fiber optic system delivers light components through fibers 208 and 210, and through lenses 216 and 214, respectively. A first light component is reflected by moving mirror 220 traveling in direction 220, and returns through fibers 210 and 212. A second light component is directed onto tissue 218, and light scattered by the tissue is returned through fibers 208 and 212. Dichroic mirror 230 separates the two wavelength $\lambda_1$ and $\lambda_2$ which are detected by detectors 240 and 242, respectively. The heterodyne detection systems 250 and 252 are used to process the detected systems as described previously in connection with FIG. 1. The systems described herein can be used in conjunction with standard endoscopics to provide diagnostic information retrieved from lumens or tissue within the human body in vivo.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of measuring a nuclear size in tissue comprising:
   irradiating a region of interest in the tissue with spatially coherent light having a first beam with a first wavelength and a second beam with a second wavelength;
   directing reference light having the first wavelength and the second wavelength along an optical path having a variable path length;
   detecting scattered light from the material in response to the irradiating light and detecting the reference light while varying the path length;
   generating a heterodyne signal from the detected scattered light and the detected reference light; and
   determining a size of a cell nucleus within the tissue using the heterodyne signal.

2. The method of claim 1 further comprising forming an image of the region of interest.

3. The method of claim 1 further comprising measuring a size of a plurality of different nuclei within a region of tissue.

4. The method of claim 1 wherein the first beam and the second beam irradiate a focal area within the region of interest.

5. The method of claim 1 further comprising measuring the tissue at a plurality of first and second wavelengths.

6. The method of claim 1 further comprising combining scattered light and the reference light and subsequently detecting the combined light.

7. The method of claim 1 further comprising measuring a refractive index of a material within a region of tissue.

8. The method of claim 1 further comprising recording data in electronic memory and comparing the data to reference data.

9. The method of claim 1 further comprising using a fiber optic device to transmit light.

10. The method of claim 1 further comprising using a low coherence light source.

11. The method of claim 1 further comprising detecting backscattered light from a region of interest.

12. The method of claim 1 further comprising adjusting a depth within the tissue being measured.

13. The method of claim 1 further comprising aligning the first beam and the second beam to overlap at the region of interest.

14. An optical system for measuring a nuclear size in tissue comprising:
   a light source and an optical system that irradiates a region of interest tissue with spatially coherent light having a first beam with a first wavelength and a second beam with a second wavelength that is harmonically related to the first wavelength;
   a reference light beam having the first wavelength and the second wavelength along an optical path having a variable path length;
   an actuator that adjusts the variable path length;
   a detector system that detects scattered light front the material in response to the irradiating light and detects the reference light while varying the path length, the detector system generating a heterodyne signal from the detected scattered light and the detected reference light; and
   a computer programmed to determine a size of cell nuclei in the tissue from the heterodyne signal.

15. The system of claim 14 further comprising a scanning assembly that scans the first beam and the second beam across the tissue such that an image of the region of interest.

16. The system of claim 14 further comprising a data processor that computes a size of size tissue structure within the region of interest.

17. The system of claim 14 wherein the first beam and the second beam irradiate a focal area within the region of interest.

18. The system of claim 14 further comprising a light source emitting a plurality of first and second wavelengths.

19. The system of claim 14 wherein the light source comprises a laser system that generates first and second wavelengths.

20. The system of claim 14 further comprising a fiberoptic probe.

21. The system of claim 14 wherein the light source comprises a wavelength tunable laser.

22. The system or claim 14 further comprising a scanner that alters a beam path through the tissue.

23. The system of claim 22 wherein the scanner alters an angle of the beam path relative to the tissue.

24. The system of claim 14 further comprising a time correlation system.

25. The system of claim 14 further comprising a fiber optic fiber optic coupler and an interferometer.

26. The system of claim 16 wherein the structure comprises a cell or a cell nucleus.

27. The system of claim 14 further comprising a computer having a memory with stored reference data.

* * * * *